United States Patent
Verhoef et al.

(10) Patent No.: US 9,603,318 B2
(45) Date of Patent: Mar. 28, 2017

(54) HYBRID TOMATO VARIETY 72-240 RZ

(71) Applicant: RIJK ZWAAN ZAADTEELT EN ZAADHANDEL B.V., De Lier (NL)

(72) Inventors: Rudolf Verhoef, Naaldwijk (NL); Johan Cornelis Solleveld, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 14/067,157

(22) Filed: Oct. 30, 2013

(65) Prior Publication Data

US 2014/0123332 A1 May 1, 2014

Related U.S. Application Data

(60) Provisional application No. 61/721,263, filed on Nov. 1, 2012.

(51) Int. Cl.
  *A01H 5/08* (2006.01)
  *A01H 1/00* (2006.01)
  *C12N 15/00* (2006.01)

(52) U.S. Cl.
  CPC .................................. *A01H 5/08* (2013.01)

(58) Field of Classification Search
  None
  See application file for complete search history.

(56) References Cited

U.S. PATENT DOCUMENTS

2011/0219472 A1* 9/2011 Heath ........................ 800/268

* cited by examiner

*Primary Examiner* — Phuong Bui
(74) *Attorney, Agent, or Firm* — Vedder Price P.C.; Thomas J. Kowalski; Deborah L. Lu

(57) ABSTRACT

The present invention relates to a *Solanum lycopersicum* seed designated 72-240 RZ, which exhibits pink colored fruits, medium sized fruits, circular shape of the fruits in longitudinal section, fruits having two or three locules. The present invention also relates to a *Solanum lycopersicum* plant produced by growing the 72-240 RZ seed. The invention further relates to methods for producing the tomato cultivar, represented by tomato variety 72-240 RZ.

18 Claims, 1 Drawing Sheet

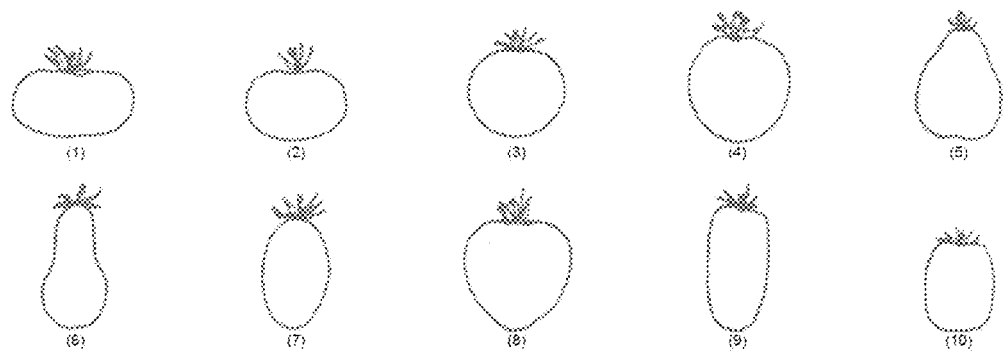

HYBRID TOMATO VARIETY 72-240 RZ

INCORPORATION BY REFERENCE

Related Applications and Incorporation by Reference

This application claims benefit of and priority to U.S. provisional patent application Ser. No. 61/721,263 filed Nov. 1, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new hybrid tomato (*Solanum lycopersicum*) variety 72-240 RZ which exhibits a combination of traits including pink colored fruits, medium sized fruits, circular shape of the fruits in longitudinal section, fruits having two or three locules.

BACKGROUND OF THE INVENTION

Tomato plants of the species *Solanum lycopersicum* belong to the nightshade family, also known as Solanaceae. Within this family it is nowadays grouped in the genus *Solanum*, which does not only harbor tomato, but also the important food crops potato and eggplant. It is a perennial, herbaceous, flowering plant species which is native to South America.

Other species that are related to tomato within the *Solanum* genus are for example *Solanum pimpinellifolium*, *Solanum chilense*, *Solanum peruvianum* and *Solanum habrochaites*. Although it is known that crossing can be considerably difficult, these species are used to obtain traits that are valuable in growing tomato. In the recent history, advancement in tomato breeding has led to tomato varieties having, for example higher yield, higher disease resistance and increased shelf life.

Tomato plants are being cultivated worldwide for their highly nutritious fruits. The tomato fruit is consumed in diverse ways, including raw, as an ingredient in many dishes and sauces, and in drinks. While it is botanically a fruit, it is considered a vegetable for culinary purposes. The fruit is rich in lycopene, which may have beneficial health effects. In 2009, the total acreage for both fresh and processing tomatoes in the United States was approximately 442,100 acres, with a total production of about 14,141,920 tons (source: USDA).

Commercial vegetable production, including the production of tomato, is affected by many conditions. The choice of the grower for a certain variety is a determining factor, and forms the genetic basis for the result that can be achieved. In addition, there are many external factors that influence the outcome. Growing conditions like climate, soil, and the use of inputs like fertilizer play a major role. There are various ways of cultivating tomatoes, among which, the most common are: open field, greenhouse and shade house production. Although the species can be grown under a wide range of climatic conditions, it performs most successfully under dry and warm conditions. In addition to this, the presence of pests and diseases also affects the total yield that can be reached.

In order to create tomato varieties that are satisfying the needs of growers and/or consumers, many considerations have to be taken into account. The goal is to combine within a single variety or hybrid an improved combination of desirable traits from the parental germplasms. These traits may include higher yield, field performance, fruit and agronomic quality such as firmness, color, content in soluble solids, acidity and viscosity, resistance to diseases and insects, and tolerance to drought and heat. With mechanical harvesting of the tomato fruits for processing purpose, i.e., juice, paste, catsup, etc., uniformity of plant characteristics such as germination, growth rate, maturity, and plant uniformity is also important.

Tomato is a simple diploid species with twelve pairs of chromosomes. The cultivated tomato is self-fertile and almost exclusively self-pollinating. The tomato flowers are hermaphrodites. Tomato cultivars were initially open-pollinated, such as many well-known heirloom tomatoes, but also varieties were developed for large scale growing facilities. Nowadays, especially in a professional growing setting these cultivars are replaced by better yielding hybrids. Due to its wide dissemination and high value, tomato has been intensively bred. This explains why such a wide array of tomatoes are now available. The size may range from small to large, and there are cherry, plum, pear, standard, and beefsteak types. Tomatoes may be grouped by the amount of time it takes for the plants to mature fruit for harvest; in general the cultivars are considered to be early, midseason or late-maturing. Tomatoes can also be grouped by the plant's growing habit, being determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants will tend to have tomato fruit in different stages of maturity at any given time. More recent developments in tomato breeding have led to a wider array of fruit color. In addition to the standard red ripe color, tomatoes can have a creamy white, lime green, pink, yellow, golden, or orange color. Also breeding for multiple disease and pest resistances is an important aspect in providing varieties for multiple growing systems and climates. These diseases can be the result of attacks of either nematodes, bacteria, fungi, viruses and/or insects. Important microorganisms causing such diseases in tomato plants and their fruits in this respect include: *Meloidogyne incognita* (Mi), *Verticillium dahliae* race 0 (Vd), *Fusarium oxysporum* f. sp. *lycopersici* race 0 (ex1) and race 1 (ex2) (Fol), *Fusarium oxysporum* f. sp. *radicis lycopersici* (For), *Cladosporium fulvum* groups A, B, C, D and E (Ff), Tomato Mosaic Virus (ToMV) strain 0, 1 and 2, *Stemphylium* spp. and Tomato Spotted Wilt Virus (TSWV).

Further, the color, shape, taste and size of the fruits that are produced by the tomato plant are relevant characteristics when breeding for commercial tomato varieties.

Pink colored tomatoes are not common and most varieties that are available are heirloom or open pollinated varieties, i.e. not hybrids. Japanese breeders and growers have a known reputation in relation to pink tomato varieties. Most of these varieties also have specific taste which is known as 'umami', also referred to as the fifth taste, besides the common tastes sweet, sour, salt and bitter. This umami taste is very popular in Japan, but also outside the country (Yamaguchi et al., Journal of Nutrition, 130(4), 921S-926S, 2000).

Most available pink tomato varieties tend to produce relatively large fruits. The size of a tomato fruit is related with the number of locules. In general it can be stated that the larger the number of locules present in one fruit, the larger the size of this fruit will be (Mañs S et al., Plant Physiol., 156(4), 2244-2254, 2011). In addition, the fruits of pink heirloom varieties show very strong ribbing at the peduncle end of the fruit, and the fruits have a flattened shape when measured in longitudinal section.

The way in which fruits from tomato plants are harvested is also relevant. When the fruits are not ripe at the same time, single harvest of fruits has to be applied in order to provide a fresh product to the consumer. In the case that fruits of one truss are ripening synchronous, the whole truss can be harvested and be marketed. To support this development, the interest for breeding of uniform ripening trusses has increased in the recent years.

Citation or identification of any document in this application is not an admission that such document is available as prior art to the present invention.

SUMMARY OF THE INVENTION

There exists a need for a hybrid tomato variety which exhibits a combination of traits including pink colored fruits, medium sized fruits, circular shape of the fruits in longitudinal section, fruits having two or three locules.

The present invention fulfills this need by providing a new tomato (*Solanum lycopersicum*) variety, designated 72-240 RZ. Tomato cultivar 72-240 RZ exhibits a combination of traits including pink colored fruits, medium sized fruits, circular shape of the fruits in longitudinal section, fruits having two or three locules.

The present invention provides seeds of tomato cultivar 72-240 RZ, which have been deposited with the National Collections of Industrial, Marine and Food Bacteria (NCIMB) in Bucksburn, Aberdeen AB21 9YA, Scotland, UK and have been assigned NCIMB Accession No. 42048.

In one embodiment, the invention provides a tomato plant which may exhibit a combination of traits including pink colored fruits, medium sized fruits, circular shape of the fruits in longitudinal section, fruits having two or three locules, representative seed of which have been deposited under NCIMB Accession No. 42048.

In one embodiment, the invention provides a tomato plant which may exhibit a combination of traits including pink colored fruits, medium sized fruits, circular shape of the fruits in longitudinal section, fruits having two or three locules, representative seed of which have been deposited under NCIMB Accession No. 42048, or tomato variety or cultivar designated 72-240 RZ, as well as seed from such a plant, plant parts of such a plant (such as those mentioned herein) and plants from such seed and/or progeny of such a plant, advantageously progeny exhibiting such combination of such traits, each of which may be within the scope of the invention; such combination of traits may also include weak ribbing at the peduncle end, absence of green shoulder before maturity and an indeterminate growth type. Preferably, the plants of the invention are suited for cluster harvesting, i.e the harvesting of complete trusses.

In one embodiment, the invention provides a tomato plant which may exhibit a combination of traits including resistance to *Verticillium dahliae* race 0 (Vd), *Fusarium oxysporum* f. sp. *lycopersici* race 0 (ext) and race 1 (ex2) (Fol), *Fusarium oxysporum* f. sp. *radicis lycopersici* (For), *Cladosporium fulvum* groups A, B, C, D and E (Ff), Tomato Mosaic Virus (ToMV) strain 0, 1 and 2, *Stemphylium* spp. and Tomato Spotted Wilt Virus (TSWV) and absence of sensitivity to silvering.

In one embodiment, the invention provides a tomato plant designated 72-240 RZ, representative seed of which have been deposited under NCIMB Accession No. 42048.

In an embodiment of the present invention, there also is provided parts of a tomato plant of the invention, which may include parts of a tomato plant exhibiting a combination of traits including pink colored fruits, medium sized fruits, circular shape of the fruits in longitudinal section, fruits having two or three locules, or parts of a tomato plant having any of the aforementioned resistance(s) and a combination of traits including one or more morphological or physiological characteristics tabulated herein, including parts of hybrid tomato variety 72-240 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come include those wherein representative seed of which has been deposited under NCIMB Accession No. 42048.

In another embodiment there is a plant grown from seeds, representative seed of which having been deposited under NCIMB Accession No. 42048. In a further embodiment there is a plant regenerated from the above-described plant parts or regenerated from the above-described tissue culture. Advantageously such a plant may have morphological and/or physiological characteristics of hybrid tomato variety 72-240 RZ and/or of a plant grown from seed, representative seed of which having been deposited under NCIMB Accession No. NCIMB 42048—including without limitation such plants having all of the morphological and physiological characteristics of hybrid tomato variety 72-240 RZ and/or of a plant grown from seed, representative seed of which having been deposited under NCIMB Accession No. NCIMB 42048. Accordingly, in still a further embodiment, there is provided a tomato plant having all of the morphological and physiological characteristics of hybrid tomato variety 72-240 RZ, representative seed of which having been deposited under NCIMB Accession No. 42048. Such a plant may be grown from the seeds, regenerated from the above-described plant parts, or regenerated from the above-described tissue culture. A tomato plant having any of the aforementioned resistance(s), and one or more morphological or physiological characteristics recited or tabulated herein, and a tomato plant advantageously having all of the aforementioned resistances and the characteristics recited and tabulated herein, are preferred. Parts of such plants—such as those plant parts above-mentioned—are encompassed by the invention.

In one embodiment, there is provided progeny of tomato cultivar 72-240 RZ produced by sexual or vegetative reproduction, grown from seeds, regenerated from the above-described plant parts, or regenerated from the above-described tissue culture of the tomato cultivar or a progeny plant thereof, representative seed of which having been deposited under NCIMB Accession No. 42048.

Progeny of the hybrid tomato variety 72-240 RZ may be modified in one or more other characteristics, in which the modification is a result of, for example and without limitation, mutagenesis or transformation with a transgene.

In still another embodiment, the present invention provides progeny of tomato cultivar 72-240 RZ produced by sexual or vegetative reproduction, grown from seeds, regenerated from the above-described plant parts, or regenerated from the above-described tissue culture of the tomato cultivar or a progeny plant thereof, in which the regenerated plant shows a combination of traits including pink colored fruits, medium sized fruits, circular shape of the fruits in longitudinal section, fruits having two or three locules.

In another embodiment the invention relates to a method of producing an inbred tomato plant derived from a plant of the invention of which representative seed has been deposited under NCIMB Accession No. NCIMB 42048, which may comprise of the steps: a) preparing a progeny plant derived from hybrid tomato variety 72-240 RZ by crossing a tomato plant exhibiting a combination of traits including pink colored fruits, medium sized fruits, circular shape of the fruits in longitudinal section, fruits having two or three locules, representative seed of which have been deposited under NCIMB Accession No. 42048 with a second tomato plant; b) crossing the progeny plant with itself or a second tomato plant to produce a seed of a progeny plant of a subsequent generation; c) growing a progeny plant of a subsequent generation from said seed and crossing the progeny plant of a subsequent generation with itself or a second tomato plant; and d) repeating step b) or c) for at least 1 more generation to produce an inbred tomato plant derived from the hybrid tomato variety 72-240 RZ.

The invention even further relates to a method of producing tomato fruits which may comprise: (a) cultivating the hybrid tomato variety 72-240 RZ, representative seed of which having been deposited under NCIMB Accession No. NCIMB 42048, to produce fruits and; (b) harvesting tomato fruits from the plant. The invention further comprehends the fruit itself, optionally in processed or packed form.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

Deposit

The Deposit with NCIMB Ltd, Ferguson Building, Craibstone Estate, Bucksburn, Aberdeen AB21 9YA, UK, on Aug. 31, 2012, under deposit accession number NCIMB 42048 was made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawing, in which:

FIG. 1 is an illustration of ten different shapes of tomato fruits.

DETAILED DESCRIPTION OF THE INVENTION

The invention provides methods and compositions relating to plants, seeds and derivatives of a new hybrid tomato variety herein referred to as hybrid tomato variety 72-240 RZ. 72-240 RZ is a hybrid plant variety that is uniform and distinct from other such hybrids, and may be stably produced after a cycle of reproduction.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant or plants. These important traits may include but are not limited to higher yield, field performance, fruit and agronomic quality such as fruit shape, color and length, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes coding for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial tomato hybrids relates to the development of tomato parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Pedigree breeding is used commonly for the improvement and development of inbred lines of self-pollinating or cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, generally the best individuals in the best families are selected. Replicated testing of families, or hybrid combinations involving individuals of these families, often follows in the F4 generation to improve the effectiveness of selection for traits with low heritability. At an advanced stage of inbreeding suitable lines are used as parents to produce F1 hybrids, which are subsequently tested for potential release as new varieties or cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g. the cultivar or parent line) and the desirable trait transferred from the donor parent. After the initial cross, individuals possessing the phenotype of the donor parent for the preferred trait are selected and repeatedly crossed (backcrossed) to the recurrent parent. The resulting plant is expected to have the attributes of the recurrent parent (e.g. the cultivar or parent line) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (Glycine max) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci may be routinely used and more alleles per marker locus may be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent.

This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into tomato varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of doubled haploids may also be used for the development of homozygous lines in a breeding program. Doubled haploids are produced by the doubling of one set of chromosomes from a heterozygous plant to produce a completely homozygous individual. For example, see Wan et al., Theor. Appl. Genet., 77:889-892, 1989.

The tomato plant of the invention may be arrived at through crossing of inbred lines or through selection of the disclosed desirable characteristics by any of the breeding and selection methods mentioned above.

Hybrid tomato variety 72-240 RZ is a cross between two uniform parent lines and made for the first time in 2011. The female line TR 1209, a uniform line from a backcross of the red line TR 5222 x (TR 5222 x the pink 06S Mom 235-1). The male line TR 5210, a uniform line from a backcross of the red line TR 5306 x (TR 5306 x the pink 06S Mom 235-1). Both parent lines were selected and developed from the initial cross until uniformity on the RZ breeding station in De Lier in The Netherlands. This breeding process resulted in a tomato variety which produces round, pink tomato fruits of a medium size, suitable for harvest of complete trusses and for growing under heated greenhouse conditions.

In one embodiment, a plant of the invention has all the morphological and physiological characteristics of tomato variety 72-240 RZ. These characteristics of a tomato plant of the invention, e.g. variety 72-240 RZ, are summarized in Table 1. In table 2 the main differences with a comparable publicly available variety are given.

The information presented in tables 1 and 2 was determined in trial experiments in accordance with official Dutch plant variety registration authorities (Naktuinbouw). The terminology used in these tables is the official terminology as used by the Dutch plant variety registration authorities (Naktuinbouw) as of the filing date, and is thus clear for a person skilled in the art.

As used herein pink is a fruit color comparable to the fruit color of the varieties "House Momotaro" and "Aichi First".

As used herein medium is a fruit size comparable to the fruit size of the varieties "Alphamech" and "Diego".

As used herein circular shape of the fruits in longitudinal section is a fruit shape comparable to the fruit shape of the varieties "Cerise" and "Moneymaker".

As used herein, the two to three locules present in fruits, is the locule number comparable to the locule number in the varieties "Alphamech" and "Futuria".

As used herein, weak ribbing at the peduncle end is the ribbing of a fruit comparable to the ribbing of a fruit of the varieties "Early Mech" and "Melody".

As used herein, the absence of green shoulders before maturity is a phenomenon comparable to the absence of green shoulders before maturity as present in the varieties "Felicia" and "Rio Grande".

As used herein, an indeterminate growth type, is a growth type comparable to the growth type of varieties "Marmande VR" and "Saint-Pierre".

The varieties that are referred to in the abovemade comparisons are varieties that are used in the "Protocol for the distinctness, uniformity and stability tests", adopted and entried in force on March 21st, 2012 by the Community Plant Variety Office (CPVO).

As used herein resistance against *Verticillium dahliae* (Vd) is the ability of a plant to resist infection by race 0 in all stages between the seedling stage and the plant stage wherein the plants bear harvestable fruits.

As used herein resistance against *Fusarium oxysporum* f. sp. *lycopersici* (Fol) is the ability of a plant to resist infection by each of the various strains race 0 (ext) and race 1 (ex2) in all stages between the seedling stage and the plant stage wherein the plants bear harvestable fruits.

As used herein resistance against *Fusarium oxysporum* f. sp. *radicis lycopersici* (For), is the ability of a plant to resist infection in all stages between the seedling stage and the plant stage wherein the plants bear harvestable fruits.

As used herein resistance against *Cladosporium fulvum* (Ff) is the ability of a plant to resist infection by each of the various strains of groups A, B, C, D and E in all stages between the seedling stage and the plant stage wherein the plants bear harvestable fruits.

As used herein resistance against Tomato Mosaic Virus (ToMV) is the ability of a plant to resist infection by each of the various strains 0, 1 and 2, in all stages between the seedling stage and the plant stage wherein the plants bear harvestable fruits.

As used herein resistance against *Stemphylium* spp is the ability of a plant to resist infection in all stages between the seedling stage and the plant stage wherein the plants bear harvestable fruits.

As used herein resistance against Tomato Spotted Wilt Virus (TSWV) is the ability of a plant to resist infection in all stages between the seedling stage and the plant stage wherein the plants bear harvestable fruits.

As used herein, the absence of sensitivity to silvering is the absence of white foliar flecking in plants, during all stages between the seedling stage and the plant stage wherein the plants bear harvestable fruits, when these plants are grown under greenhouse conditions, optionally under low temperatures.

Embodiments of the invention advantageously have one or more, and most advantageously all, of these characteristics.

TABLE 1

Physiological and morphological characteristics
of hybrid tomato variety 72-240 RZ.
Variety description information for 72-240 RZ General:

| | |
|---|---|
| Type: | Round pink |
| Usage: | Fresh market or garden |
| Type of culture: | Under glass, staked |

Plant:

| | |
|---|---|
| Growth type: | Indeterminate |
| Height: | Medium |

Leaf:

| | |
|---|---|
| Division of blade: | Bipinnate |
| Intensity of green color: | Medium |

Peduncle

| | |
|---|---|
| Abscission layer: | Present |

Fruit:

| | |
|---|---|
| Size: | Medium (100 g.) |
| Shape in longitudinal section: | Circular (FIG. 1, type 3) |
| Ribbing at peduncle end: | Weak |
| Number of locules: | Two or three |
| Green shoulder (before maturity) | Absent |
| Color (at maturity): | Pink |
| Firmness | Medium |
| Time of maturity: | Medium |
| Shelf-life | Medium (2.5 weeks) |

Disease and pest resistances:

| | |
|---|---|
| Sensitivity to silvering | Absent |
| *Meloidogyne incognita* (Mi) | Susceptible |
| *Verticillium dahliae* race 0 (Vd) | Present |
| *Fusarium oxysporum* f. sp. *lycopersici* race 0 (ex1) (Fol) | Present |
| *Fusarium oxysporum* f. sp. *lycopersici* race 1 (ex2) (Fol) | Present |
| *Fusarium oxysporum* f. sp. *radicis lycopersici* (For) | Present |
| *Cladosporium fulvum* (Ff) group A | Present |
| *Cladosporium fulvum* (Ff) group B | Present |
| *Cladosporium fulvum* (Ff) group C | Present |
| *Cladosporium fulvum* (Ff) group D | Present |
| *Cladosporium fulvum* (Ff) group E | Present |
| Tomato Mosaic Virus (ToMV) strain 0 | Present |
| Tomato Mosaic Virus (ToMV) strain 1 | Present |
| Tomato Mosaic Virus (ToMV) strain 2 | Present |
| *Stemphylium* spp. | Present |
| Tomato Spotted Wilt Virus (TSWV) | Present |

TABLE 2

Comparison of 72-240 RZ with Pink Brandywine.
Variety description information for Pink Brandywine General:

| | |
|---|---|
| Type: | Pink beefsteak |
| Usage: | Fresh market or garden |
| Type of culture: | Under glass, staked |

Plant:

| | |
|---|---|
| Growth type: | Indeterminate |
| Height: | Medium |

Leaf:

| | |
|---|---|
| Division of blade: | Pinnate |
| Intensity of green colour: | Medium |

Peduncle

| | |
|---|---|
| Abscission layer: | Present |

Fruit:

| | |
|---|---|
| Size: | Large (200 g.) |
| Shape in longitudinal section: | Flattened |
| Ribbing at peduncle end: | Very strong |
| Number of locules: | More than six |
| Green shoulder (before maturity) | Present |
| Color (at maturity): | Pink |
| Firmness | Medium |
| Time of maturity: | Late |
| Shelf-life | Medium (2 weeks) |

In an embodiment, the invention relates to tomato plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced into a hybrid by backcrossing the trait into one or both parents, useful traits may be introduced directly into the plant of the invention, being a plant of hybrid tomato variety 72-240 RZ, by genetic transformation techniques; and, such plants of hybrid tomato variety 72-240 RZ that have additional genetic information introduced into the genome or that express additional traits by having the DNA coding therefore introduced into the genome via transformation techniques, are within the ambit of the invention, as well as uses of such plants, and the making of such plants.

Genetic transformation may therefore be used to insert a selected transgene into the plant of the invention, being a plant of hybrid tomato variety 72-240 RZ or may, alternatively, be used for the preparation of transgenes which may be introduced by backcrossing. Methods for the transformation of plants, including tomato, are well known to those of skill in the art.

Vectors used for the transformation of tomato cells are not limited so long as the vector may express an inserted DNA in the cells. For example, vectors which may comprise promoters for constitutive gene expression in tomato cells (e.g., cauliflower mosaic virus 35S promoter) and promoters inducible by exogenous stimuli may be used. Examples of suitable vectors include pBI binary vector. The "tomato cell" into which the vector is to be introduced includes various forms of tomato cells, such as cultured cell suspensions, protoplasts, leaf sections, and callus. A vector may be introduced into tomato cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target tomato cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of tomato variety 72-240 RZ.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including tomato plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from tomato (psaD, psaF, psaE, PC, FNR, atpC, atpD, cab, rbcS) (see U.S. Pat. No. 7,161,061), the CAB-1 promoter from tomato (see U.S. Pat No. 7,663,027), the promoter from maize prolamin seed storage protein (see U.S. Pat No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the tomato variety of this invention include, for example, DNA sequences or genes from another species, or even genes or sequences which originate from or are present in tomato species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of tomato variety 72-240 RZ. Non-limiting examples of particular genes and corresponding phenotypes one may choose to introduce into a tomato plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat No. 7,576,262, "Modified gene-silencing RNA and uses thereof")

U.S. Pats. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed tomato and/or methods of transforming tomato or tomato plant cells, and techniques from these US Patents, as well as promoters, vectors, etc., may be employed in the practice of this invention to introduce exogenous nucleic acid sequence(s) into a plant of tomato variety 72-240 RZ (or cells thereof), and exemplify some exogenous nucleic acid sequence(s) which may be introduced into a plant of tomato variety 72-240 RZ (or cells thereof) of the invention, as well as techniques, promoters, vectors etc., to thereby obtain further plants of tomato variety 72-240 RZ, plant parts and cells, seeds, other propagation material, harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. Tissue culture methodologies relating to tomato plants are well known in the art (Girish-Chandel et al., Advances in Plant Sciences, 13: 1, 11-17 (2000); Costa et al., Plant Cell Report, 19: 3 327-332 (2000); Plastira et al., Acta Horticulturae, 447, 231-234 (1997); Zagorska et al., Plant Cell Report, 17: 12 968-973 (1998); Asahura et al., Breeding Science, 45: 455-459 (1995); Chen et al., Breeding Science, 44: 3, 257-262 (1994); Patil et al., Plant and Tissue and Organ Culture, 36: 2, 255-258 (1994). In vitro regeneration of Solanaceae cultivars is further described in Schuelter A. R. et al. Genet. Mol. Res. 2009 Aug 11;8(3):963-75, In vitro regeneration of cocona (*Solanum sessiliflorum*, Solanaceae) cultivars for commercial production.

In vitro flowering and fruiting for tomato is described in Rao et al.: J. Plant Physiol. 2005 August; 162(8):959-62. Induction of multiple shoots from leaf segments, in vitroflowering and fruiting of a dwarf tomato (*Lycopersicon esculentum*). Further aspects of in vitro propagation of tomato plant and related families are described in Zelcer et al. Plant Cell Reports, 2(5), 252-254 (1983) Shoot regeneration in root cultures of Solanaceae; S. Shrivastava, P. K. Dubey, Int. J. of Biotechnology & Biochemistry, 3(1), 1-8 (2007) In-vitro callus induction and shoot regeneration in *Withania somnifera* Dunal; R. P. Niedz et al. Plant Science 39(3), 199-204 (1985) Plant regeneration from leaf protoplasts of six tomato cultivars.

Various other aspects of tissue culture in tomato are described and summarized in Bhatia et al. Plant Cell, Tissue and Organ Culture 78(1), 1-21 (2004) Tissue Culture Studies of Tomato (*Lycopersicon esculentum*)

Also, the invention comprehends methods for producing a seed of a "72-240 RZ"-derived tomato plant which may comprise (a) crossing a plant of tomato variety 72-240 RZ, representative seed of which having been deposited under NCIMB Accession No. NCIMB 42048, with a second tomato plant, and (b) whereby seed of a "72-240 RZ"-derived tomato plant form (e.g., by allowing the plant from the cross to grow to produce seed). Such a method may further comprise (c) crossing a plant grown from "72-240 RZ"-derived tomato seed with itself or with a second tomato plant to yield additional "72-240 RZ"-derived tomato seed, (d) growing the additional "72-240 RZ"-derived tomato seed of step (c) to yield additional "72-240 RZ"-derived tomato plants, and (e) repeating the crossing and growing of steps (c) and (d) for an additional 3-10 generations to further generate "72-240 RZ"-derived tomato plants.

The invention additionally provides a method of introducing a desired trait into a plant of hybrid tomato variety 72-240 RZ by reverse breeding (See generally allowed U.S. application Ser. No. 10/487,468, published as 2006-0179498 A1), which may comprise the following steps: (a) allowing the hybrid tomato plant to produce haploid cells, while suppressing recombination, (b) growing haploid cells into diploid plants, (c) selecting those homozygous plants which together constitute the hybrid variety of the invention as parent plants for the said hybrid, (d) crossing one of the said parent plants with a plant having the desired trait, (e) crossing the selected F1 progeny with said parent plant, to produce backcross progeny; (f) selecting backcross progeny which may comprise the desired trait and the physiological and morphological characteristic of the parent plant; and, optionally, (g) repeating steps (e) and (f) one or more times in succession to produce selected fourth or higher backcross progeny that comprise the desired trait and all of the physiological and morphological characteristics of said parent plant, (h) crossing the backcrossed parent plant having the added desired trait with the other parent plant obtained after reverse breeding to obtain a plant which may comprise the desired trait and all of the physiological and morphological characteristics of a plant of tomato variety 72-240 RZ.

Backcrossing one of the parents of a hybrid may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention further involves a method of determining the genotype of a plant of tomato variety 72-240 RZ, representative seed of which has been deposited under NCIMB Accession No. NCIMB 42048, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of tomato variety 72-240 RZ.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphsims of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

The invention is further described by the following numbered paragraphs:

1. Tomato plant exhibiting a combination of traits including pink colored fruits, medium sized fruits, circular shape of the fruits in longitudinal section, fruits having two or three locules, representative seed of which having been deposited under NCIMB Accession No. 42048.

2. Tomato plant of paragraph 1 wherein said combination of traits also includes [weak ribbing at the peduncle end and absence of green shoulder before maturity].

3. Tomato plant designated 72-240 RZ, representative seed of which having been deposited under NCIMB Accession No. 42048.

4. A seed of the plant of paragraph 1 or 2.

5. Parts of the plant of paragraph 1 or paragraph 2 or paragraph 3, wherein said parts of the plant are suitable for sexual reproduction.

6. Parts of the plant of paragraph 5, said parts selected from the group consisting of microspores, pollen, ovaries, ovules, embryo sacs and egg cells.

7. Parts of the plant of paragraph 1 or paragraph 2 or paragraph 3, wherein said parts of the plant are suitable for vegetative reproduction.

8. Parts of paragraph 7, said parts selected from the group consisting of cuttings, roots, stems, cells and protoplasts.

9. A tissue culture of regenerable cells from the tomato plant of paragraph 1 or 2.

10. A tissue culture of paragraph 9, wherein said cells or protoplasts of the tissue culture are derived from a tissue selected from the group consisting of leaves, pollen, embryos, cotyledon, hypocotyls, meristematic cells, roots, root tips, anthers, flowers, seeds and stems.

11. Progeny of a tomato plant of paragraph 1 or paragraph 2 or paragraph 3.

12. Progeny of paragraph 11, wherein said progeny is produced by sexual or vegetative reproduction of said tomato plant, and wherein said progeny exhibits a combination of traits including pink colored fruits, medium sized fruits, circular shape of the fruits in longitudinal section, fruits having two or three locules.

13. Progeny of a tomato plant of paragraph 3, having all the morphological and physiological characteristics of the tomato plant of paragraph 3, representative seed of which having been deposited under NCIMB Accession No. 42048 as found in tomato variety 72-240 RZ, representative seed of which having been deposited under NCIMB Accession No. 42048.

14. Progeny of a tomato plant of paragraph 1 or paragraph 2 or paragraph 3, representative seed of which having been deposited under NCIMB Accession 42048, and is modified in one or more other characteristics.

15. Progeny of paragraph 14, wherein the modification is effected by mutagenesis.

16. Progeny of paragraph 14, wherein the modification is effected by transformation with a transgene.

17. A method of producing an inbred tomato plant derived from hybrid tomato variety 72-240 RZ, comprising the steps:
   a) preparing a progeny plant derived from hybrid tomato variety 72-240 RZ by crossing the plant of paragraph 1 or 2 with a second tomato plant;
   b) crossing the progeny plant with itself or a second tomato plant to produce a seed of a progeny plant of a subsequent generation;
   c) growing a progeny plant of a subsequent generation from said seed and crossing the progeny plant of a subsequent generation with itself or a second tomato plant; and
   d) repeating step b) or c) for at least 1 more generation to produce an inbred tomato plant derived from the hybrid tomato variety 72-240 RZ.

18. An inbred tomato plant produced by the method of paragraph 17.

19. A method of producing a tomato fruit comprising: (a) obtaining a plant according to paragraph 1 or 2, wherein the plant has been cultivated to develop fruit; and (b) collecting a tomato fruit from the plant.

20. A fruit produced by the method of paragraph 19.

21. A method for producing a seed of a 72-240 RZ-derived tomato plant comprising (a) crossing a plant of tomato variety 72-240 RZ, representative seed of which having been deposited under NCIMB Accession No. NCIMB 42048, with a second tomato plant, and (b) whereby seed of a 72-240 RZ-derived tomato plant form.

22. The method of paragraph 21 further comprising (c) crossing a plant grown from 72-240 RZ-derived tomato seed with itself or with a second tomato plant to yield additional 72-240 RZ-derived tomato seed, (d) growing the additional 72-240 RZ-derived tomato seed of step (c) to yield additional 72-240 RZ-derived tomato plants, and (e) repeating the crossing and growing of steps (c) and (d) to generate further 72-240 RZ-derived tomato plants.

23. The method of paragraph 21 or 22 wherein the 72-240 RZ-derived tomato plant exhibits a combination of traits including pink colored fruits, medium sized fruits, circular shape of the fruits in longitudinal section, fruits having two or three locules.

24. Seed produced by the method of paragraphs 21 or 22 or 23.

25. A method of introducing a desired trait into a plant of hybrid tomato variety 72-240 RZ comprising:
(a) crossing a parent plant of hybrid tomato variety 72-240 RZ, with a second tomato plant that comprises the desired trait to produce F1 progeny;
(b) selecting an F1 progeny that comprises the desired trait;
(c) crossing the selected F1 progeny with said parent plant of tomato variety 72-240 RZ, to produce backcross progeny and
(d) selecting backcross progeny comprising the desired trait and the physiological and morphological characteristic of said parent plant of tomato variety 72-240 RZ, when grown in the same environmental conditions.

26. The method of paragraph 25 wherein the parent plant is obtained by reverse breeding.

27. A method of determining the genotype of a plant of tomato variety 72-240 RZ, representative seed of which has been deposited under NCIMB Accession No. NCIMB 42048, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of tomato variety 72-240 RZ.

28. The method of paragraph 27 additionally comprising the step of storing the results of detecting the plurality of polymorphisms on a computer readable medium, or transmitting the results of detecting the plurality of polymorphisms.

29. The computer readable medium of paragraph 28.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A tomato plant designated 72-240 RZ, representative seed of which having been deposited under NCIMB Accession No. 42048.

2. A seed that produces the plant of claim 1.

3. A part of the plant of claim 1, wherein said part of the plant is suitable for sexual reproduction.

4. The part of the plant as claimed in claim 3, wherein said part comprises a microspore, pollen, ovary, ovule, embryo sac or egg cell.

5. A part of the plant of claim 1, wherein said part of the plant is suitable for vegetative reproduction.

6. The part as claimed in claim 1, wherein said part comprises a cutting, root, stem, cell or protoplast.

7. A tissue culture of regenerable cells or protoplasts from the tomato plant of claim 1.

8. The tissue culture as claimed in claim 7, wherein said cells or protoplasts of the tissue culture are obtained from a tissue comprising a leaf, pollen, cotyledon, hypocotyl, meristematic cell, root, root tip, anther, flower, or stem.

9. A tomato plant having all the morphological and physiological characteristics of the tomato plant of claim 1, wherein the morphological and physiological characteristics are as found in tomato variety 72-240 RZ, representative seed of which having been deposited under NCIMB Accession No. 42048.

10. A method of producing a tomato plant obtained from hybrid tomato variety 72-240 RZ, comprising:
a) preparing a progeny plant obtained from hybrid tomato variety 72-240 RZ by crossing the plant of claim 1 with itself or a second tomato plant to obtain the progeny plant;
b) crossing the progeny plant with itself or a second tomato plant to produce a seed of a progeny plant of a subsequent generation;
c) growing a progeny plant of the subsequent generation from said seed and crossing the progeny plant of the subsequent generation with itself or a second tomato plant; and
d) repeating steps b) and c) for at least 1 more generation to obtain a further progeny tomato plant obtained from the hybrid tomato variety 72-240 RZ.

11. A method of producing a tomato fruit comprising:
(a) obtaining the plant according to claim 1, wherein the plant has been cultivated to develop fruit; and
(b) collecting a tomato fruit from the plant.

12. A fruit produced by the method of claim 11, wherein the fruit comprises all of the morphological and physiological characteristics of hybrid tomato variety 72-240 RZ.

13. A method for producing a seed of a 72-240 RZ-derived tomato plant comprising
(a) crossing a plant of tomato variety 72-240 RZ, representative seed of which having been deposited under NCIMB Accession No. 42048, with a second tomato plant, and
(b) obtaining seed of a 72-240 RZ-derived tomato plant.

14. The method of claim 13 further comprising
(c) crossing a plant grown from 72-240 RZ-derived tomato seed with itself or with a second tomato plant to yield additional 72-240 RZ-derived tomato seed,
(d) growing the additional 72-240 RZ-derived tomato seed of step (c) to yield additional 72-240 RZ-derived tomato plants, and
(e) repeating the crossing and growing of steps (c) and (d) to generate further 72-240 RZ-derived tomato plants.

15. The method of claim 14 wherein the further 72-240 RZ-derived tomato plant exhibits a combination of traits including pink colored fruits, medium sized fruits, circular shape of the fruits in longitudinal section, and fruits having two or three locules.

16. A method of determining the genotype of a plant of tomato variety 72-240 RZ, representative seed of which has been deposited under NCIMB Accession No. 42048, or a first generation progeny thereof, comprising obtaining a sample of nucleic acids from said plant, or said first generation progeny thereof, comparing said nucleic acids to a sample of nucleic acids obtained from a reference plant, and detecting a plurality of polymorphisms between the two nucleic acid samples, thereby determining the genotype of the plant.

17. The method of claim 16 additionally comprising the step of storing the results of detecting the plurality of polymorphisms on a computer readable medium, or transmitting the results of detecting the plurality of polymorphisms to a computer readable medium.

18. The tomato plant of claim 1, which is a plant grown from seed having been deposited under NCIMB Accession No. 42048.

\* \* \* \* \*